(12) United States Patent
Hastings et al.

(10) Patent No.: US 10,417,370 B2
(45) Date of Patent: Sep. 17, 2019

(54) CLASSICAL SIMULATION CONSTANTS AND ORDERING FOR QUANTUM CHEMISTRY SIMULATION

(71) Applicant: Microsoft Technology Licensing, LLC, Redmond, WA (US)

(72) Inventors: Matthew Hastings, Santa Barbara, CA (US); David Wecker, Redmond, WA (US)

(73) Assignee: Microsoft Technology Licensing, LLC, Redmond, WA (US)

( * ) Notice: Subject to any disclaimer, the term of this patent is extended or adjusted under 35 U.S.C. 154(b) by 493 days.

(21) Appl. No.: 15/118,476

(22) PCT Filed: Feb. 6, 2015

(86) PCT No.: PCT/US2015/014700
§ 371 (c)(1),
(2) Date: Aug. 11, 2016

(87) PCT Pub. No.: WO2015/123085
PCT Pub. Date: Aug. 20, 2015

(65) Prior Publication Data
US 2017/0177782 A1 Jun. 22, 2017

Related U.S. Application Data

(60) Provisional application No. 61/939,196, filed on Feb. 12, 2014.

(51) Int. Cl.
*G06F 17/50* (2006.01)
*G06N 10/00* (2019.01)
*B82Y 10/00* (2011.01)

(52) U.S. Cl.
CPC ........ *G06F 17/5077* (2013.01); *G06N 10/00* (2019.01); *B82Y 10/00* (2013.01)

(58) Field of Classification Search
USPC ........................................................ 716/104
See application file for complete search history.

(56) References Cited

U.S. PATENT DOCUMENTS 7,135,701 B2   11/2006  Amin et al.
8,229,863 B2    7/2012  Amin et al.
(Continued)

FOREIGN PATENT DOCUMENTS

CN    1755715 A    4/2006

OTHER PUBLICATIONS

Whitfield, James; Biamonte, Jacob; Aspuru-Guzik, Alan; "Simulation of Electronic Structure Hamiltonians Using Quantum Computers," arXiv:1001.3855 [quant-ph]; Dec. 19, 2010 (Year: 2010).*
(Continued)

*Primary Examiner* — Eric D Lee
(74) *Attorney, Agent, or Firm* — Klarquist Sparkman, LLP

(57) ABSTRACT

Quantum computations based on second quantization are performed by applying one body and two body terms in a selected order. Typically, terms associated with operators that commute are applied prior to application of other terms. In a particular example, one body terms of the form $h_{pp}$ are applied first, followed by two body terms of the form $h_{prrp}$.

20 Claims, 7 Drawing Sheets

(56) References Cited

U.S. PATENT DOCUMENTS

| | | |
|---|---|---|
| 8,301,390 B2 | 10/2012 | Sastry et al. |
| 2003/0121028 A1 | 6/2003 | Coury et al. |
| 2003/0164490 A1 | 9/2003 | Blais |
| 2006/0123363 A1 | 6/2006 | Williams et al. |

OTHER PUBLICATIONS

Office Action issued in Chinese Patent Application No. 201580008058.3, dated Feb. 11, 2018, 9 pages. (MS# 340923-CN-PCT).

Abbott et al., "Understanding the Quantum Computational Speed-Up via De-Quantisation," Electronic Proceedings in Theoretical Computer Science, 12 pages (Mar. 2010).

Brown et al., "Using Quantum Computers for Quamum Simulation," Journal of Entropy, 43 pages (Nov. 2010).

International Preliminary Report on Patentabililty from International Application No. PCT/US2015/014700, dated Apr. 28, 2016, 6 pages.

International Search Report and Written Opinion from International Application No. PCT/US2015/014700, dated Sep. 3, 2015, 13 pages.

Jones et al., "Faster quantum chemistry simulation on fault-tolerant quantum computers," *New Journal of Physics*, 14:1-35 (Nov. 27, 2012).

Kassal et al., "Simulating Chemistry Using Quantum Computers," *Annu. Rev. Phys. Chem.*, 62:185-207 (2011).

Sampson et al., "Utilization of Variable Reordering in Quantum ESCT Minimization," 9th Hellenic European Research on Computer Mathmatics and its Applications Conference, 7 pages (Sep. 2009).

Viamontes, "Efficient Quantum Circuit Simulation," Disseratation of Doctor of Philosophy at The University of Michigan, Retrieved on: Dec. 31, 2013, Available at http://web.eecs.umich.edu/~imarkov/pubs/diss/GFVdiss.pdf.

Viamontes et al., "High-Performance QuIDD-Based Simulation of Quantum Circuits," Design, Automation and Test in Europe Conference and Exhibition vol. 2, 2 pages (Feb. 16, 2004).

Wecker et al., "Can quantum chemistry be performed on a small quantum computer?," arXiv preprint arXiv:1312.1695, 13 pages (Dec. 5, 2013).

Wecker et al., "Can quantum chemistry be performed on a small quantum computer?" available at: http://arxiv.org/pdf/1312.1695v2.pdf, 15 pages (Jan. 6, 2014).

Wecker, "Language-Integrated Quantum Operations: A Software Architecture for Quantum Computing," Retrieved on: Dec. 31, 2013, Available at: http://research.microsoft.com/apps/video/default.aspx?id=194277.

Whitefield et al., "Simulation of electronic structure Hamiltonians using quantum computers," *Molecular Physics*, 109:735-750 (Mar. 2011).

Written Opinion of the International Preliminary Examining Authority from International Application No. PCT/US2015/014700, dated Jan. 18, 2016, 7 pages.

* cited by examiner

CLASSICAL SIMULATION CONSTANTS AND ORDERING FOR QUANTUM CHEMISTRY SIMULATION

CROSS REFERENCE TO RELATED APPLICATIONS

This is the U.S. National Stage of International Application No. PCT/US2015/014700, filed Feb. 6, 2015, which was published in English under PCT Article 21(2), which in turn claims the benefit of U.S. Provisional Application No. 61/939,196, filed Feb. 12, 2014. The provisional application is incorporated herein in its entirety.

FIELD

The disclosure pertains to quantum computations for chemical systems.

BACKGROUND

One application of quantum computing is in the evaluation of quantum systems. For example, the properties of complex chemical compounds have been identified as suitable for determination using quantum computation. Generally, materials whose properties are based on quantum evaluation of many body interactions can be assessed using quantum computing. Unfortunately, conventional computational approaches generally require repeated application of products of complex exponentials that are based on a Hamiltonian associated with the system of interest. So-called Trotter-Suzuki expansions are used, but errors in these expansions arise because the operators associated with these products generally do not commute. Thus, conventional approaches have inherent errors that can occur regardless of Trotter-Suzuki step size.

SUMMARY

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

Quantum circuits and methods and apparatus for quantum circuit design are based on defining a first set of quantum circuits associated with one-body and two-body Hamiltonian coefficients associated with commuting operators. The first set of quantum circuits includes one or more gates that apply a controlled-Z rotation based on such Hamiltonian coefficients. A second set of quantum circuits is defined based on one-body and two-body Hamiltonian coefficients associated with non-commuting operators. The second set of quantum circuits includes one or more gates that apply a control-Z rotation based on such Hamiltonian coefficients. The first and second sets of quantum circuits are arranged so that a plurality of qubits is coupled to the first set of quantum circuits prior to coupling to the second set of quantum circuits. For applications based on second quantization, one body Hamiltonian coefficients of the form $h_{pp}$ and two body coefficients of the form $h_{prrp}$ are used in defining the first set of circuits, wherein p and r are integers denoting spin orbitals. Values of Hamiltonian coefficients associated with non-commuting operators can be adjusted based on a number of Trotter-Suzuki steps. For example, in applications based on second quantization, one-body Hamiltonian coefficients of the form $h_{pq}$ ($p \neq q$) and two body Hamiltonian coefficients of the form $h_{pqrs}$ ($q \neq r$) can be adjusted, wherein p, q, r and s are integers denoting spin orbitals.

The foregoing and other features and advantages of the disclosed technology will become more apparent from the following detailed description, which proceeds with reference to the accompanying figures.

DETAILED DESCRIPTION

Figure 1:
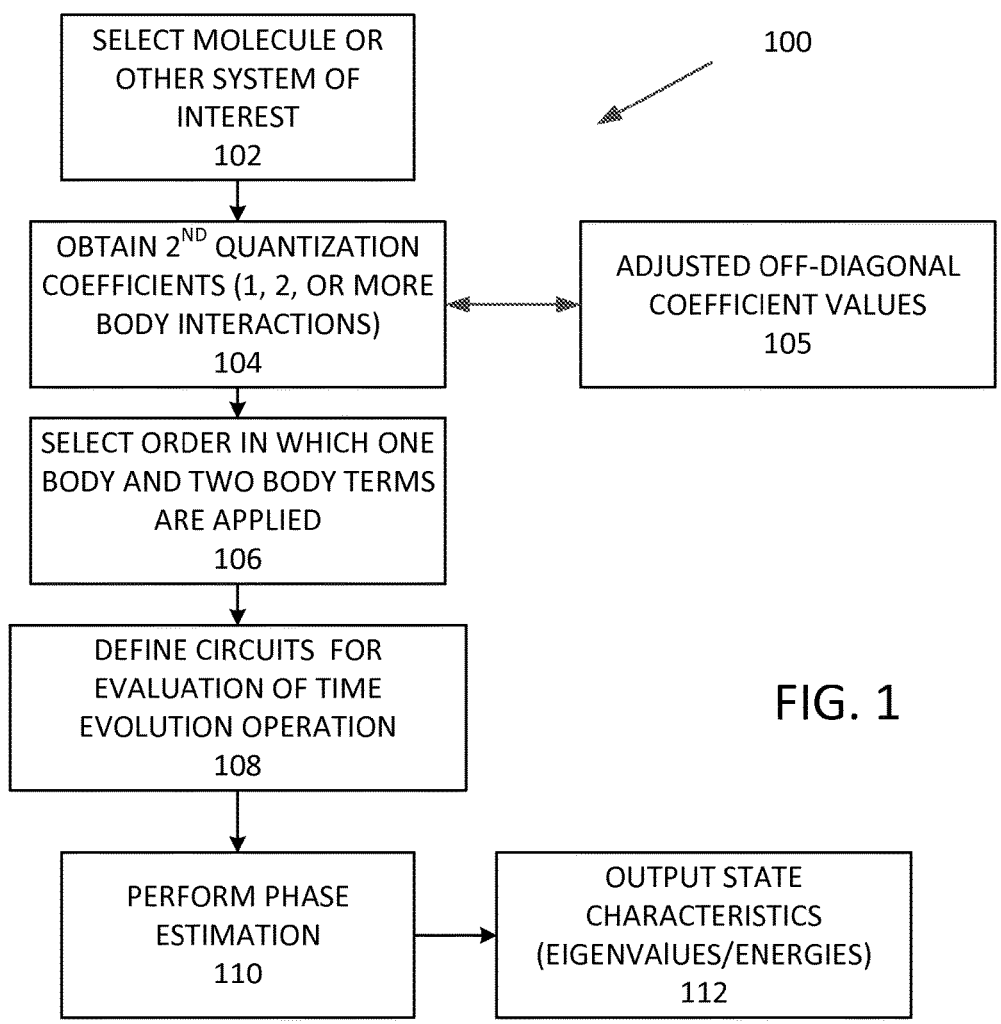
FIG. 1 illustrates a representative procedure for quantum chemical computations using quantum computing circuits.

As used in this application and in the claims, the singular forms "a," "an," and "the" include the plural forms unless the context clearly dictates otherwise. Additionally, the term "includes" means "comprises." Further, the term "coupled" does not exclude the presence of intermediate elements between the coupled items.

The systems, apparatus, and methods described herein should not be construed as limiting in any way. Instead, the present disclosure is directed toward all novel and non-obvious features and aspects of the various disclosed embodiments, alone and in various combinations and sub-combinations with one another. The disclosed systems, methods, and apparatus are not limited to any specific aspect or feature or combinations thereof, nor do the disclosed systems, methods, and apparatus require that any one or more specific advantages be present or problems be solved. Any theories of operation are to facilitate explanation, but the disclosed systems, methods, and apparatus are not limited to such theories of operation.

Although the operations of some of the disclosed methods are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed systems, methods, and apparatus can be used in conjunction with other systems, methods, and apparatus. Additionally, the description sometimes uses terms like "produce" and "provide" to describe the disclosed methods. These terms are high-level abstractions of the actual operations that are performed. The actual operations that correspond to these terms will vary depending on the particular implementation and are readily discernible by one of ordinary skill in the art.

In some examples, values, procedures, or apparatus' are referred to as "lowest", "best", "minimum," or the like. It will be appreciated that such descriptions are intended to indicate that a selection among many used functional alternatives can be made, and such selections need not be better, smaller, or otherwise preferable to other selections The disclosed methods and apparatus can be applied to systems based on a variety of physical implementations of qubits such as those based on trapped ions, cold atoms, Josephson junction devices, solid state spin, Majorana fermions, photon polarization, among others. In some applications, so-called topologically protected qubits are preferred to provide fault tolerance.

The disclosed methods and apparatus generally pertain to quantum computation based on a second-quantized Hamiltonian associated with a material of interest. The second-quantized Hamiltonian can be mapped to qubits, and logical states of each qubit can be associated with occupancy of a single-electron spin-orbital, wherein 0 denotes occupied, and 1 denotes unoccupied. A system with N single-electron spin-orbitals can be represented with N qubits. Systems with any numbers of electrons up to N can be represented using N qubits. In other representations, larger numbers of qubits can be used.

The Jordan Wigner transformation can be used to transform creation and annihilation operators so as to be represented using Pauli spin matrices. While a general time-evolution operator for a multi-body system may not be readily representable as a sequence of gates, a Hamiltonian can be expressed as a sum of one and two-electron terms whose time-evolution operators can each be implemented using a sequence of gates. The associated unitary time evolution operator can be approximated using Trotter-Suzuki relations based on time-evolution of non-commuting operators Quantum computations for multi-body systems can be conveniently stated in a so-called second quantization form, wherein a Hamiltonian operator H is expressed as:

$$H = \sum_m h_{pq} p^\dagger q + \sum_m h_{pqrs} p^\dagger q^\dagger rs, \quad (1)$$

wherein p, q, r, and s identify molecular orbitals, with each molecular orbital occupied by either a spin-up or spin-down particle, or both or neither. The $h_{pq}$ and $h_{pqrs}$ values are amplitudes associated with such particles; terms with a dagger (†) correspond to particle creation and terms without a dagger refer to particle annihilation. The $h_{pq}$ and $h_{pqrs}$ values can be obtained exactly or can be estimated. For example using a Hartree-Fock procedure, $$h_{pq} = \int d\vec{x} \chi_p^*(\vec{x}) \left( -\frac{1}{2} \nabla^2 - \sum \frac{Z_\alpha}{r_{\alpha x}} \right) \chi_q(\vec{x}), \text{ and}$$

$$h_{pqrs} = \int d\vec{x}_1 d\vec{x}_2 \frac{\chi_p^*(\vec{x}_1)\chi_q^*(\vec{x}_2)\chi_r(\vec{x}_2)\chi_s(\vec{x}_1)}{r_{12}},$$

wherein the integrals are performed over volume coordinates associated with x, $\chi_p(x)$ denotes a single particle basis function, $r_{\alpha x}$ and $r_{12}$ are distances between the $\alpha^{th}$ nucleus and the electron and the distance between electrons 1 and 2, respectively. A variety of basis functions can be used as deemed appropriate for a particular system of interest.

For convenient description, the $h_{pq}$ and $h_{pqrs}$ values are referred to herein as one-body Hamiltonian coefficients and two-body Hamiltonian coefficients, respectively, that couple basis states p and q and p, q, r, and s, respectively, wherein p, q, r, and s, are integers. These one-body and two-body Hamiltonian coefficients can be obtained in a variety of different ways using, for example, conventional computer programs that carry out computations such as those above. Coefficients obtained in any manner can be used in the examples below.

In many simulations, a unitary time-evolution operator U(t) corresponding to a product of exponentials of each of the terms in the second quantized representation of the Hamiltonian is used. The time evolution operator U(t) for a system having a Hamiltonian $$H = \sum_{i=1}^{N} \hat{h}_i,$$

can be expressed as:

$$U(t) = e^{iHt} = (e^{i\hat{h}_1 t} e^{i\hat{h}_2 t} \ldots e^{i\hat{h}_N t}).$$

Using the second quantized form of the Hamiltonian, the time-evolution of a state ψ(0) can be expressed as:

$$\psi(t) = \Pi e^{-iH_{pq}t} \Pi e^{-iH_{pqrs}t} \psi(0).$$

The above forms are exact only so long as all of the operators $H_{pq}$ and $H_{pqrs}$ commute. If any operators do not commute, results obtained by application of the combined operator depends on the order in which the operators are applied.

Errors associated with non-commutative operators can be reduced using a Trotter-Suzuki expansion. For example, a time evolution operator for a system associated with non-commutating operators A and B can be expressed as:

$$e^{A+B} = (e^{A/n} e^{B/n})^n,$$

which is exact for n→∞. In typical quantum computing approaches, each term in a product of exponentials of operators is associated with a corresponding quantum circuit. Thus, if non-commutation errors are to be reduced using a large value of n, circuits must be executed n times as well. This can significantly increase circuit complexity. As disclosed herein, errors introduced by non-commutating operators can be reduced by selecting a suitable order of operations.

Referring to FIG. 1, a method 100 of computing quantum characteristics includes selecting a molecule, compound, or material of interest at 102. At 104, interaction terms corresponding to one-body and two-body Hamiltonian coefficients ($h_{pq}$ and $h_{pqrs}$, respectively) are determined based on, for example, second quantization. In some cases, off-diagonal values of these coefficients are adjusted at 105. An order of application of the one-body and two-body Hamiltonian coefficients terms (with or without adjustment) is selected at 106. Quantum circuits that correspond to system time evolution based on those coefficients are defined at 108 and arranged in a suitable order. With the arranged circuits, phase estimates, control-Z rotations, or other procedures are executed at 110. At 112, one or more computed values are output, one or more eigenvalues (i.e., energies) associated with at least one state of the material of interest, typically a ground state energy.

Figure 2:
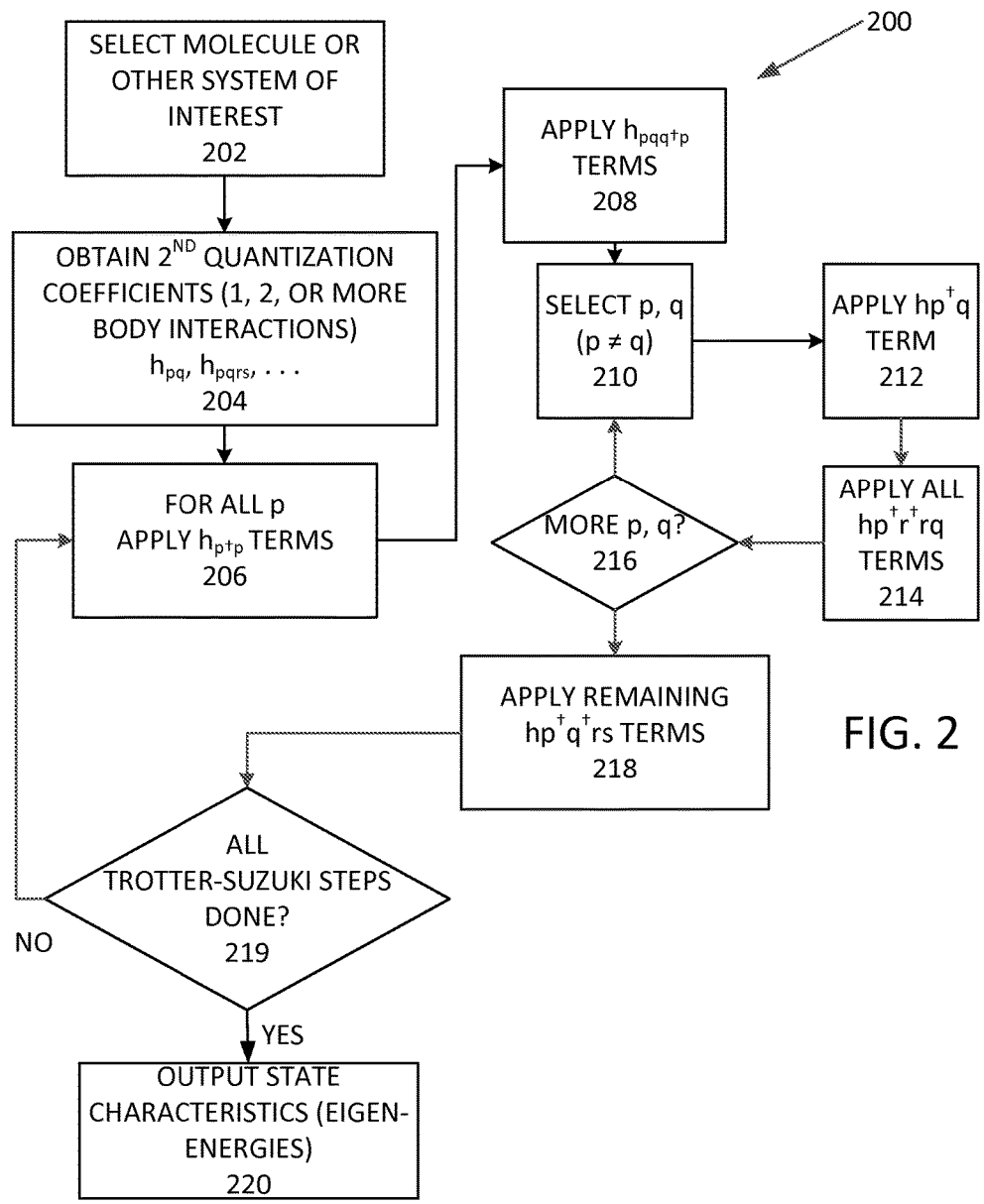
FIG. 2 illustrates a representative method of applying second quantization Hamiltonian coefficients in a quantum computer.

FIG. 2 illustrates a quantum computing method 200. At 202, a molecule or other system of interest is selected. At 204, second quantization Hamiltonian coefficients $h_{pq}$, $h_{pqrs}$ are obtained based on one and two-body interactions. (As noted above, off-diagonal terms can be adjusted, if desired.) The obtained terms are then applied as follows. At 206, operations corresponding to the Hamiltonian terms $h_{pq}$, i.e., $e^{-ih_{pq}t}$, are applied for p=q. These terms are associated with operators that are commutative and can be done in any order without introducing error. At 208, operations corresponding to two body Hamiltonian coefficients of the form $h_{pqqp}$ are applied. At 210, basis states identified with integers p and q, with p≠q are selected, and at 212, operators associated with the one-body Hamiltonian coefficients $h_{pq}$ are applied followed by application of operators associated with the two-body Hamiltonian coefficients $h_{prrq}$ at 214. At 216, the values of p, q are assessed to determine if additional values are available that have not yet been used. If so, the steps 210, 212, 214, 216 are repeated until all possible p, q values with p≠q are used. At 218 operators associated with any remaining two-body Hamiltonian terms $h_{pqrs}$ are applied. If all Trotter-Suzuki steps are completed as determined at 219, output state characteristics (typically a ground state energy) are output at 220. Otherwise, a subsequent Trotter-Suzuki iteration is initiated by returning to step 206. In most applications, the Hamiltonian coefficients are repeated based on a number of Trotter-Suzuki steps (all using steps 206 through 218), but only a single such step is shown in FIG. 2.

Figure 3:
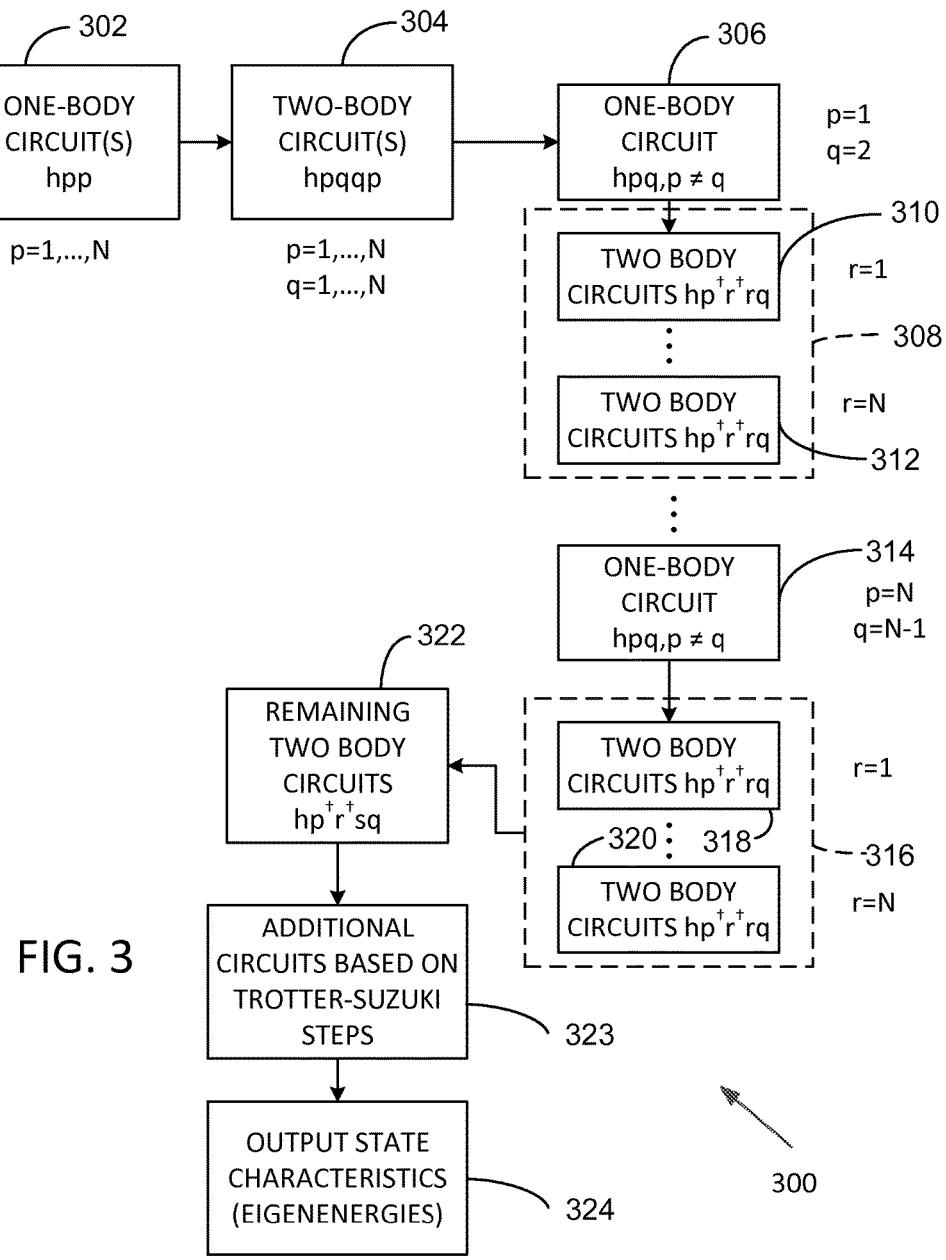
FIG. 3 illustrates a representative arrangement of quantum circuits for applying second quantization Hamiltonian coefficients.

A representative quantum circuit 300 is illustrated in FIG. 3 for computation using a total of N orbitals. A plurality 302 of one body circuits is defined by one body Hamiltonian coefficients of the form $h_{pp}$. Generally, all available coefficients are used, so that circuits for each of $h_{11}, \ldots, h_{NN}$ are included. However, one or more terms can be omitted if small or for other reasons. A plurality 304 of two body circuits is defined by two body Hamiltonian coefficients of the form $h_{pqqp}$. Generally, all available coefficients are used, so that circuits for each of $h_{1111}$, $h_{1221}$, ..., $h_{1NN1}$, $h_{2112}$, ..., $h_{2NN2}$, ..., $h_{N11N}$, ..., $h_{NNNN}$ are included. Of course, not all coefficients need be represented. A circuit 306 is based on the one-body Hamiltonian coefficient $h_{pq}$ (p=1, q=2) and is coupled to a series of two-body circuits 308 that includes circuits associated with two-body Hamiltonian coefficients of the form $h_{pqqp}$. FIG. 3 shows only representative circuits 310, 312 that are based on two-body Hamiltonian coefficients $h_{1112}$, $h_{1NN2}$, respectively. Additional circuits associated with one-body Hamiltonian coefficients $h_{pq}$ for p≠q and two-body Hamiltonian coefficients of the form $h_{pqqp}$ are included as well. For purposes of illustration, additional circuits for p=N and q=N-1 are shown. Circuit 314 is associated with a one-body Hamiltonian coefficient $h_{N(N-1)}$, and a plurality 316 of two-body circuits is based on two-body Hamiltonian coefficients of the form $h_{Nrr(N-1)}$. Representative circuits 318, 320 associated with two-body Hamiltonian coefficients $h_{N11(N-1)}$, $h_{NNN(N-1)}$ are shown. A plurality 322 of circuits is associated with remaining two-body Hamiltonian coefficients. Additional circuits 323 similar to these circuits and in the same arrangement are included based on a selected number of Trotter-Suzuki steps, but are not shown in further detail in FIG. 3. A measurement circuit 324 provides an output associated with Hamiltonian characteristics, generally an energy associated with a ground state or other state.

Figure 4A:
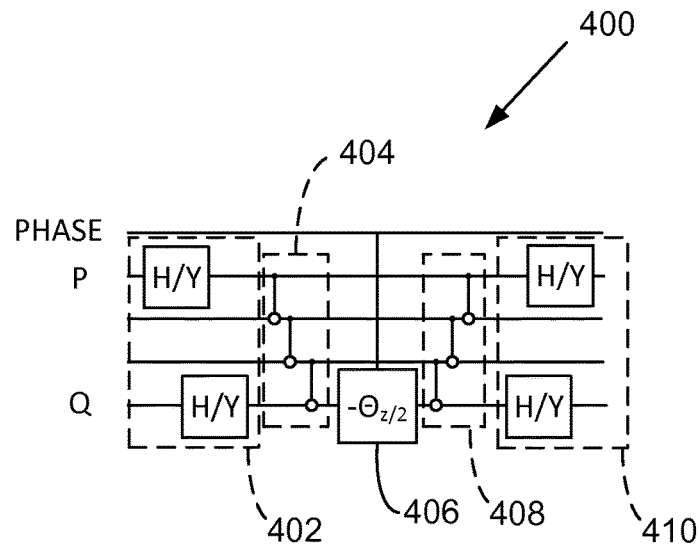
FIGS. 4A-4B illustrate representative quantum circuits that can be used to apply second quantization Hamiltonian coefficients.

FIG. 4A illustrates a circuit 400 arranged based on a one-body Hamiltonian coefficient associated with orbitals P and Q. A first set 402 of basis change gates, shown as Hadamard gates (H) or Pauli Y-gates (Y) is coupled to qubits associated with P and Q. A first set 404 of entanglement gates (C-NOT gates) is coupled to the qubits, and a control rotation in Z (control-Z) gate 406 is arranged to apply a control-Z rotation associated with a selected one-body Hamiltonian coefficient. A second set 408 of entanglement gates and a second set 410 of basis change gates are also included, to undo the changes produced by the first set 402 of entanglement gates and the first set 404 of basis change gates.

The arrangement of gates shown in the circuit 400 of FIG. 4A is only one example of a suitable circuit for representing a one-body Hamiltonian coefficient. In particular, entanglement gates and basis change gates can be arranged in other ways, and each one-body circuit need not include such gates. In addition, rotations (shown in as $-\theta_{z/2}$) based on one-body Hamiltonian coefficients can be applied with two or more control-Z gates and not just the single control-Zgate 406 shown in FIG. 4A. More or fewer qubits can be used as well.

Figure 4B:
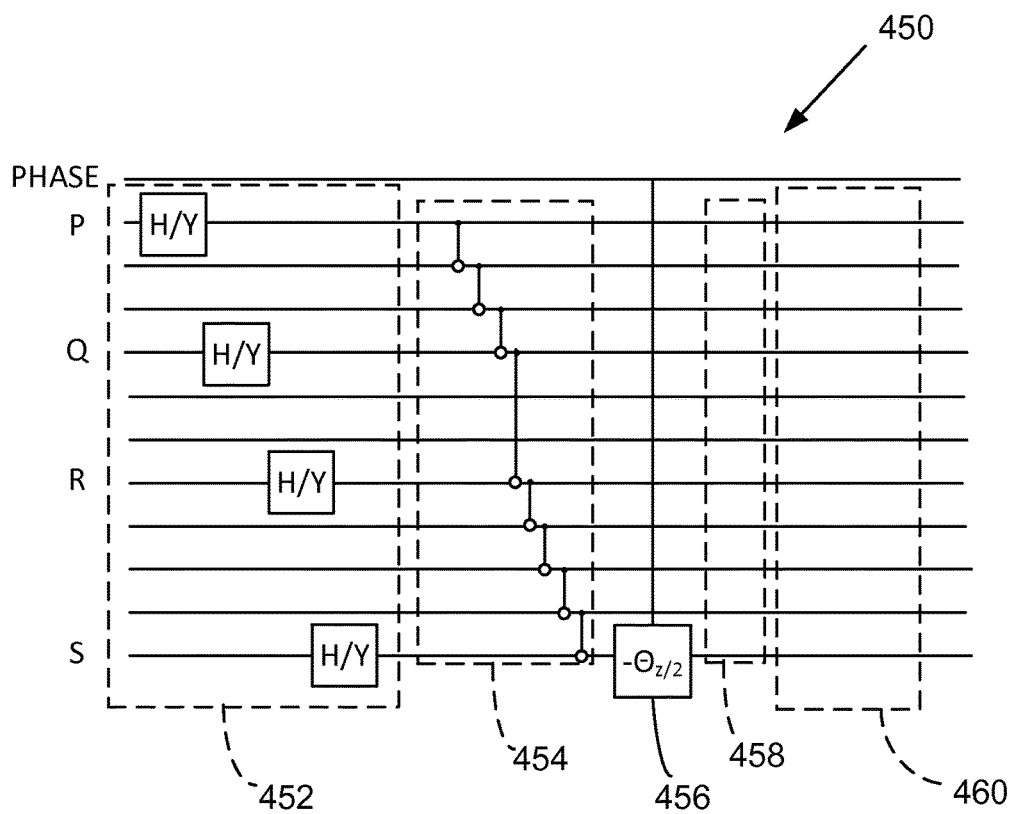

FIG. 4B illustrates a circuit 450 arranged based on a two-body Hamiltonian coefficient associated with orbitals P, Q, R, and S. A first set 452 of basis change gates, shown as Hadamard gates (H) or Pauli Y-gates (Y) is coupled to qubits associated with P, Q, R, and S. A first set 454 of entanglement gates (C-NOT gates) couples the P, Q, R, and S qubits, and a control-Z gate 456 is arranged to apply a rotation associated with a selected two-body Hamiltonian coefficient. A second set 458 of entanglement gates and a second set 460 of basis change gates are also included (shown schematically), to undo the changes produced by the first set 452 of entanglement gates and the first set 454 of basis change gates.

The arrangement of gates shown in the circuit 450 of FIG. 4B is only one example of a suitable circuit for representing a two-body Hamiltonian coefficient. In particular, entanglement gates and basis change gates can be arranged in other ways, and each one-body circuit need not include such gates. In addition, rotations based on two-body Hamiltonian coefficients can be applied with two or more rotation gates and not just the single rotation gate 456 shown in FIG. 4B. More or fewer qubits can be used as well. In some cases, basis change gates and entanglement gates for a plurality of one-body and/or two body Hamiltonian coefficients are combined to eliminate unnecessary gates or eliminate unnecessary application of CNOT or basis change gates.

Figure 5:
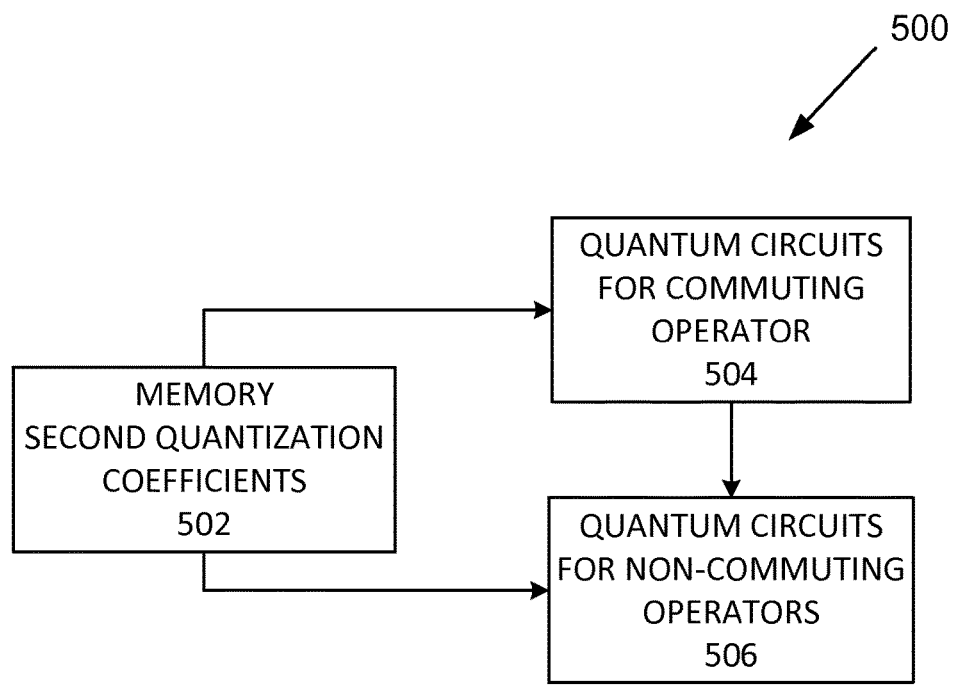
FIG. 5 is a schematic drawing of a representative quantum circuit implementing the disclosed methods.

Referring to FIG. 5, a quantum circuit 500 can be defined based on second quantization coefficients associated with a plurality of molecular orbitals. These coefficients can be stored in a conventional memory device 502 such as random access memory. The memory device 502 is coupled to a first set of quantum circuits 504 that is defined based on second quantization coefficients that are associated with commuting operators. The memory device 502 is also coupled to a second set 506 of quantum circuits that are defined based on one or more non-commuting operators associated with one or more of the second quantization coefficients. The circuits 504, 506 are arranged so that qubits are coupled to the circuits 504 and then to the circuits 506.

The second-quantized Hamiltonian can be mapped to qubits. The logical states of each qubit can be associated with occupancy of a single-electron spin-orbital, wherein 0 denotes occupied, and 1 denotes unoccupied. A system with N single-electron spin-orbitals can be represented with N qubits. Systems with any numbers of electrons up to N can be represented using N qubits. In other representations, larger numbers of qubits can be used.

In addition to improvements in computational efficiency and accuracy using the orderings above, some or all values of non-commutative or off-diagonal terms $h_{pqrs}$ for spin orbitals denoted by integers p, q, r, s with p≠s and q≠r can be updated based on values of the diagonal terms ($h_{pp}$, $h_{prrp}$,). The updated values can be better suited for use with the Quantum Full Configuration Interaction (QFCI) method for use with a quantum computer in contrast to values for use in simulations with classical computers. For a system that can be described with a Hamiltonian H=A+B wherein A is larger (in some cases, much larger) than B and A represents diagonal (commuting) terms in H and B represents off diagonal (non-commuting) terms in H, values of B can be adjusted. For example, for the second quantization Hamiltonian coefficients discussed above, define energy differences $\omega_{pq}$, $\omega_{pqrs}$ and perturbations $\varepsilon_x$ as follows:

$$\omega_{pq} = \varepsilon_p - \varepsilon_q$$

$$\omega_{pqrs} = \varepsilon_p + \varepsilon_q - \varepsilon_r - \varepsilon_s$$

$$\varepsilon_x = h_{xx} + \sum_{y(occupied)} h_{xyyx} + h_{yxxy}.$$

Only the occupied orbitals are of interest, and the corresponding $h_{pq}$, $h_{pqrs}$ values can be updated as:

$$h_{pq} \leftarrow h_{pq} f(\Delta_t \omega_{pq}), p \neq q, \text{ and}$$

$$h_{pqrs} \leftarrow h_{pqrs} f(\Delta_t \omega_{pqrs}), p \neq s,$$

wherein $$\Delta_t = \frac{2\pi}{n(\text{energy}_{max} - \text{energy}_{min})},$$

and n is a number of Trotter-Suzuki steps. The function $f$ is defined as:

$$f(x) = \sqrt{\frac{2(1-\cos(x))}{x \sin x}}.$$

The value $f(0)$ is defined as $\lim_{x \leftarrow 0} f(x) = 1$. Such adjustments of the off-diagonal values as described above can provide accuracy improvements of factors of 2-3, with or without reordering.

Representative Computing Environments

Figure 6:
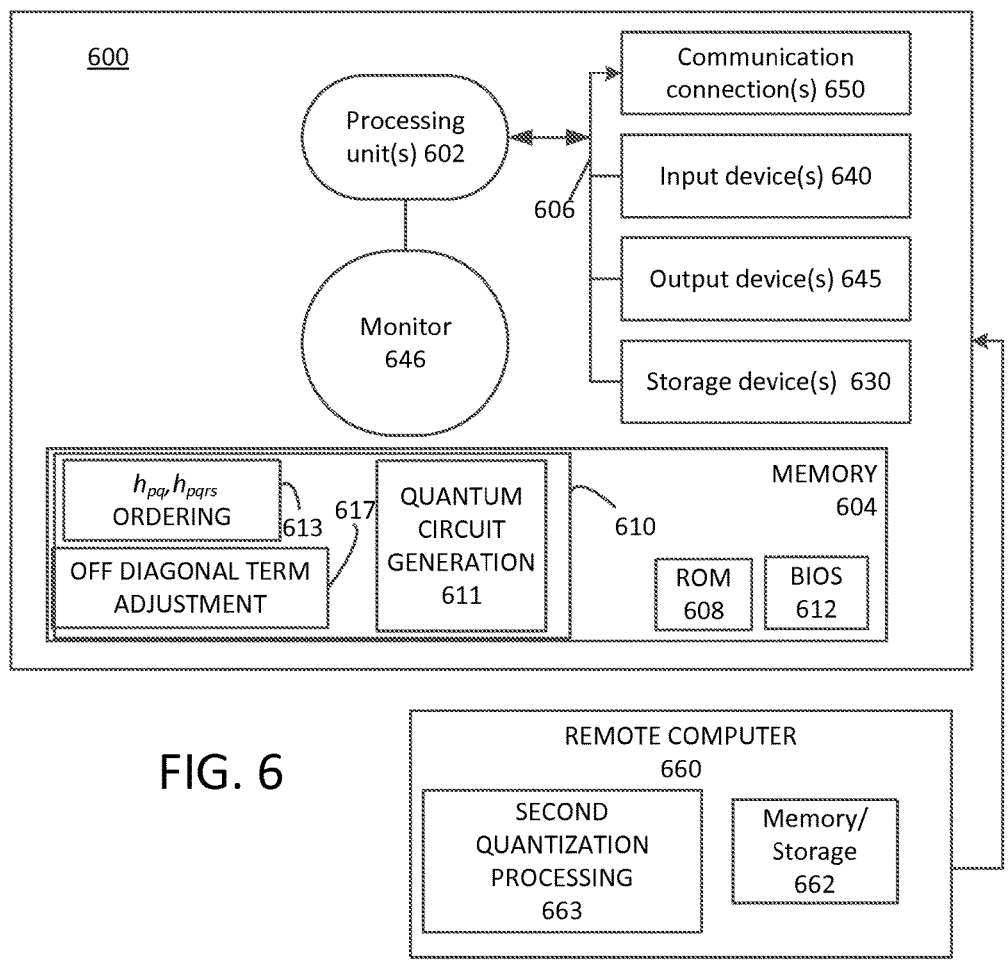
FIG. 6 illustrates an exemplary computing environment in which the disclosed technology may be implemented.

FIG. 6 and the following discussion are intended to provide a brief, general description of an exemplary computing environment in which the disclosed technology may be implemented. Although not required, the disclosed technology is described in the general context of computer executable instructions, such as program modules, being executed by a personal computer (PC). Generally, program modules include routines, programs, objects, components, data structures, etc., that perform particular tasks or implement particular abstract data types. Moreover, the disclosed technology may be implemented with other computer system configurations, including hand held devices, multiprocessor systems, microprocessor-based or programmable consumer electronics, network PCs, minicomputers, mainframe computers, and the like. The disclosed technology may also be practiced in distributed computing environments where tasks are performed by remote processing devices that are linked through a communications network. In a distributed computing environment, program modules may be located in both local and remote memory storage devices.

With reference to FIG. 6, an exemplary system for implementing the disclosed technology includes a general purpose computing device in the form of an exemplary conventional PC 600, including one or more processing units 602, a system memory 604, and a system bus 606 that couples various system components including the system memory 604 to the one or more processing units 602. The system bus 606 may be any of several types of bus structures including a memory bus or memory controller, a peripheral bus, and a local bus using any of a variety of bus architectures. The exemplary system memory 604 includes read only memory (ROM) 608 and random access memory (RAM) 610. A basic input/output system (BIOS) 612, containing the basic routines that help with the transfer of information between elements within the PC 600, is stored in ROM 608. As shown in FIG. 6, RAM 610 can store computer-executable instructions at 611 for defining and coupling quantum circuits such as quantum circuits implementing application of one or more terms in a second quantization representation of a Hamiltonian, as well as other quantum circuit functions and procedures. For example, computer executable instructions that specify an order in which such Hamiltonian terms are applied can be stored in a memory portion 613 and computer executable instructions that perform adjustments of non-diagonal terms based on computer executable instructions can be stored in a memory portion 617. In addition, some functions and procedures can be selected for implementation in conventional (non-quantum) computing hardware.

The exemplary PC 600 further includes one or more storage devices 630 such as a hard disk drive for reading from and writing to a hard disk, a magnetic disk drive for reading from or writing to a removable magnetic disk, and an optical disk drive for reading from or writing to a removable optical disk (such as a CD-ROM or other optical media). Such storage devices can be connected to the system bus 606 by a hard disk drive interface, a magnetic disk drive interface, and an optical drive interface, respectively. The drives and their associated computer readable media provide nonvolatile storage of computer-readable instructions, data structures, program modules, and other data for the PC 600. Other types of computer-readable media which can store data that is accessible by a PC, such as magnetic cassettes, flash memory cards, digital video disks, CDs, DVDs, RAMs, ROMs, and the like, may also be used in the exemplary operating environment.

A number of program modules may be stored in the storage devices 630 including an operating system, one or more application programs, other program modules, and program data. Storage of quantum syntheses and instructions for obtaining such syntheses can be stored in the storage devices 630. For example, circuits for evaluating materials based on second quantization can be defined by a quantum computer design application and circuit definitions can be stored for use in design. A user may enter commands and information into the PC 600 through one or more input devices 640 such as a keyboard and a pointing device such as a mouse. Other input devices may include a digital camera, microphone, joystick, game pad, satellite dish, scanner, or the like. These and other input devices are often connected to the one or more processing units 602 through a serial port interface that is coupled to the system bus 606, but may be connected by other interfaces such as a parallel port, game port, or universal serial bus (USB). A monitor 646 or other type of display device is also connected to the system bus 606 via an interface, such as a video adapter. Other peripheral output devices, such as speakers and printers (not shown), may be included. In some cases, a user interface is display so that a user can input a circuit for synthesis, and verify successful synthesis.

The PC 600 may operate in a networked environment using logical connections to one or more remote computers, such as a remote computer 660. In some examples, one or more network or communication connections 650 are included. The remote computer 660 may be another PC, a server, a router, a network PC, or a peer device or other common network node, and typically includes many or all of the elements described above relative to the PC 600, although only a memory storage device 662 has been illustrated in FIG. 6. In the example of FIG. 6, the remote computer 660 includes a memory 663 that includes computer-executable instructions for the determination of second quantization Hamiltonian coefficients, but can also include computer executable instructions for coefficient ordering and off-diagonal term adjustment. The personal computer 600 and/or the remote computer 660 can be connected to a local area network (LAN) and a wide area network (WAN). Such networking environments are commonplace in offices, enterprise wide computer networks, intranets, and the Internet. As shown in FIG. 6, the remote computer 660 includes computer-executable instructions that are stored in memory device 663 for obtaining a second quantization representation of a Hamiltonian for a selected material When used in a LAN networking environment, the PC 600 is connected to the LAN through a network interface. When used in a WAN networking environment, the PC 600 typically includes a modem or other means for establishing communications over the WAN, such as the Internet. In a networked environment, program modules depicted relative to the personal computer 600, or portions thereof, may be stored in the remote memory storage device or other locations on the LAN or WAN. The network connections shown are exemplary, and other means of establishing a communications link between the computers may be used.

Figure 7:
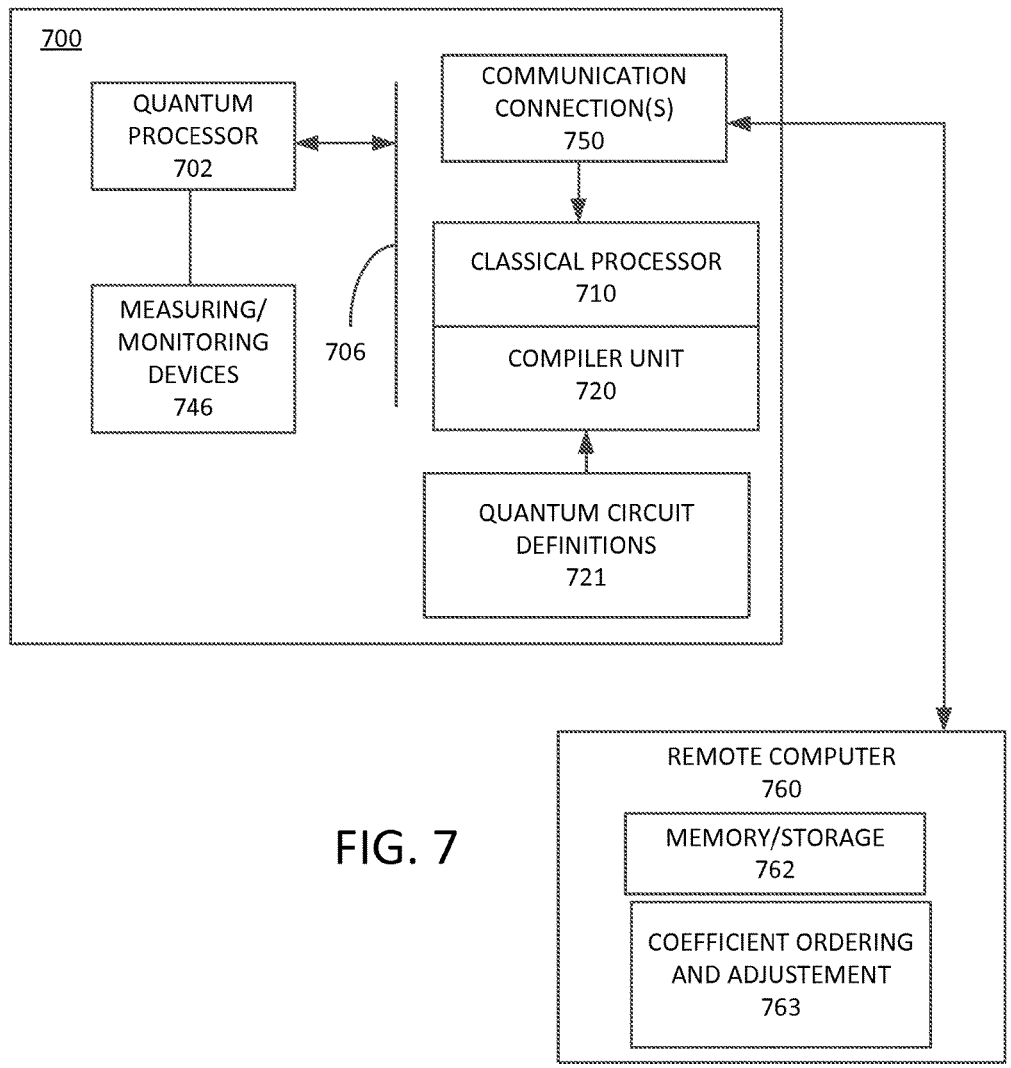
FIG. 7 illustrates, an exemplary system for compilation into quantum circuits and subsequent quantum processing using the compiled circuits.

With reference to FIG. 7, an exemplary system for implementing the disclosed technology includes computing environment 700, where compilation into quantum circuits is separated from quantum processing that uses the compiled circuits. The environment includes a quantum processing unit 702 and one or more monitoring/measuring device(s) 746. The quantum processor executes quantum circuits that are precompiled by classical compiler unit 720 using one or more classical processor(s) 710. The precompiled quantum circuits are downloaded into the quantum processing unit via quantum bus 706. In some cases, quantum circuits or portions thereof are predefined and stored as quantum circuit definitions in a memory 721. For example, quantum circuits associated with second quantization representations of Hamiltonians, applied as described above, or other functions and procedures or portions thereof can be stored in a library. A classical computer can be arranged to control a quantum computer or one or more quantum circuits thereof. The classical computer can receive the output of a classical or quantum computer. Based on the received output, the classical computer indicates which quantum circuits are to be used in subsequent quantum computations, provides definitions of suitable quantum circuits, or, in some cases, controls additional classical computations.

With reference to FIG. 7, the compilation is the process of translation of a high-level description of a quantum algorithm into a sequence of quantum circuits. Such high-level description may be stored, as the case may be, on one or more external computer(s) 760 outside the computing environment 700 utilizing one or more memory and/or storage device(s) 762, then downloaded as necessary into the computing environment 700 via one or more communication connection(s) 750. The high-level description can be stored and interpreted classically, and a classical computer can control the sequence of gates defined in a quantum computer. The high level description also controls application of gates based on initial, intermediate, or final data values. In one example, a memory and/or storage device 763 stores computer executable instructions for coefficient ordering and adjustment as described above. Such instructions can also be provided to the classical processor 710.

In view of the many possible embodiments to which the principles of the disclosed invention may be applied, it should be recognized that the illustrated embodiments are only preferred examples of the invention and should not be taken as limiting the scope of the invention. The examples above are based on second quantization for convenient illustration, but the disclosed methods and apparatus are application to higher order analyses as well. The scope of the invention is defined by the following claims. We therefore claim as our invention all that comes within the scope and spirit of these claims.

The invention claimed is:

1. A computer executable method for designing a quantum circuit for computation using a plurality of qubits, the method comprising:
    defining a first set of quantum circuits based on one-body Hamiltonian coefficients, the set including one or more gates that apply control-Z rotations based on corresponding one-body Hamiltonian coefficients of the form $h_{pp}$, wherein p is an integer denoting a spin orbital;
    defining a second set of quantum circuits based on two-body Hamiltonian coefficients, the set including one or more gates that apply control-Z rotations based on corresponding two-body Hamiltonian coefficients of the form $h_{prrp}$, wherein r is an integer denoting a spin orbital; and
    arranging first and second sets of quantum circuits based on the definitions of the first and second sets of quantum circuits so that a plurality of qubits is coupled to the first set of quantum circuits prior to coupling to the second set of quantum circuits.

2. The method of claim 1, further comprising defining a third set of quantum circuits based on a one-body Hamiltonian coefficients, the set including one or more gates that apply control-Z rotations based on corresponding one-body Hamiltonian coefficients of the form $h_{pq}$, wherein q is an integer denoting a spin orbital and p≠q, and situating a third set of quantum circuits based on the definition of the third set of quantum circuits so as to be coupled to the qubits after the first and second sets of gates.

3. The method of claim 1, further comprising:
    defining a third set of quantum circuits based on one-body Hamiltonian coefficients and two-body Hamiltonian coefficients, the set including one or more gates that apply control-Z rotations based on corresponding one-body and two-body Hamiltonian coefficients, wherein gates that apply control-Z rotations associated with two-body Hamiltonian coefficients of the form $h_{prrq}$, wherein q is an integer denoting a spin orbital, p≠q, follow gates that apply control-Z rotations based on corresponding one-body Hamiltonian coefficients of the form $h_{pq}$; and situating a third set of quantum circuits based on the definition of the third set of quantum circuits so as to be coupled to the qubits after the second set of quantum circuits.

4. The method of claim 3, further comprising:

defining a fourth set of quantum circuits based on two-body Hamiltonian coefficients, the set including one or more gates that apply control-Z rotations based on corresponding two-body Hamiltonian coefficients, wherein the one or more gates apply control-Z rotations associated with two-body Hamiltonian coefficients of the form $h_{prsq}$, wherein s is an integer denoting a spin orbital and r≠s; and arranging a fourth set of quantum circuits based on the definition of the fourth set of quantum circuits so as to follow the third set of quantum circuits.

5. The method of claim 3, wherein the first set of quantum circuits includes gates corresponding to one or more of a number operator, an excitation operator, a Coulomb and exchange operator, a number-excitation operator, and a double-excitation operator.

6. The method of claim 1, further comprising defining a first series of entanglement gates associated with the first set of quantum circuits and a second series of entanglement gates associated with the second set of quantum circuits, wherein the entanglement gates of the first series and the second series are situated so as to be applied to the qubits prior to application of the first set of quantum circuits and the second set of quantum circuits, respectively.

7. The method of claim 1, further comprising defining at least a first series of basis change gates associated with the first set of quantum circuits and at least a second series of basis change gates associated with the second series of quantum circuits, wherein the basis change gates of the first series and the second series are situated so as to be applied to the qubits prior to application of the first set of quantum circuits and the second set of quantum circuits, respectively.

8. The method of claim 7, wherein the basis change gates are Hadamard gates, Pauli-Y gates, and Pauli-X gates, or combinations thereof.

9. The method of claim 1, further comprising:

selecting at last one Hamiltonian coefficient of the form $h_{pq}$, p≠q or $h_{pqrs}$, q≠r, wherein q and s are integers denoting spin orbitals; and adjusting the value of the selected at least one Hamiltonian coefficient.

10. The method of claim 9, wherein the selected at least one Hamiltonian coefficient is adjusted based on one or more Hamiltonian coefficients of the form $h_{pp}$ and $h_{prrq}$.

11. The method of claim 9, wherein the value is adjusted based on a number of Trotter-Suzuki steps.

12. An apparatus for specifying a quantum computing circuit, comprising:

a memory device storing one-body and two-body Hamiltonian coefficients associated with a material of interest; and a processor that:

receives the stored one-body and two-body Hamiltonian coefficients;

selects an order in which quantum gates associated with the stored one-body and two-body Hamiltonian coefficients $h_{pq}$, $h_{pqrs}$, respectively are to be applied to a plurality of qubits, wherein p, q, r, s are integers identifying orbitals, such that coefficients are applied in the order $h_{pp}$, for all p, $h_{prrp}$, for all p and r; and defines a sequence of quantum gates based on the order.

13. The apparatus of claim 12, wherein the order is selected such that gates associated with Hamiltonian coefficients $h_{pq}$ and $h_{prrq}$, wherein p q, follow gates associated with the Hamiltonian coefficients $h_{pp}$, for all p and $h_{prrp}$, for all r.

14. The apparatus of claim 12, further wherein the selected order includes the Hamiltonian coefficients $h_{pp}$, for all p and $h_{prrp}$, for all r, followed by alternating pairs of Hamiltonian coefficients of the form $h_{pq}$, $h_{prrq}$.

15. The apparatus of claim 14, wherein the selected order includes Hamiltonian coefficients of the form $h_{pq}$, wherein p≠s and q≠r.

16. The apparatus of claim 12, wherein the sequence of quantum gates includes entanglement gates and basis change gates.

17. The apparatus of claim 16, wherein the entanglement gates are CNOT gates, and the basis change gates are Hadamard gates, Pauli-X gates, and Pauli-Y gates, or combinations thereof.

18. The apparatus of claim 12, wherein the processor adjusts values of at least some Hamiltonian coefficient associated with non-commuting operators.

19. The apparatus of claim 18, where the adjusted values are based on a number of Trotter-Suzuki steps.

20. A quantum circuit, comprising:

a first series of quantum gates defined based on one-body Hamiltonian coefficients associated with a material of interest, the Hamiltonian coefficients corresponding to commuting operators, wherein the first series of quantum gates is defined based on one-body Hamiltonian coefficients of the form $h_{pp}$, wherein p is an integer denoting an orbital; and an intermediate series of quantum gates defined based on one-body and two-body Hamiltonian coefficients of the forms $h_{pq}$, $h_{prrq}$, respectively, wherein p, q, r, s are integers denoting orbitals and p≠q, and the series includes alternating pairs of gates $h_{pq}$, $h_{prrq}$ for at least some values of p, q, r; and a second series of quantum gates defined based on one-body or two-body Hamiltonian coefficients associated with the material of interest, wherein the Hamiltonian coefficients are non-commutative, wherein the second series of quantum gates is defined based on two-body Hamiltonian coefficients of the form $h_{pqrs}$, wherein p, q, r, s are integers denoting orbitals and p≠s and q≠r; and wherein the first series of quantum gates, the intermediate series of quantum gates, and the second series of quantum gates are situated so that the first series precedes the intermediate series and the intermediate series precedes the second series.

* * * * *